United States Patent [19]

Sakoda et al.

[11] 4,188,343
[45] Feb. 12, 1980

[54] PROCESS FOR PREPARING ANTHRANYLALDEHYDE DERIVATIVES

[75] Inventors: Ryozo Sakoda; Isao Hashiba; Kazuo Nagano, all of Funabashi, Japan

[73] Assignee: Nissan Chemical Industries, Ltd., Tokyo, Japan

[21] Appl. No.: 973,599

[22] Filed: Dec. 27, 1978

[51] Int. Cl.² .................... C07C 91/161; C07C 91/28
[52] U.S. Cl. ............................ 260/571; 260/566 R; 562/452; 562/456; 562/457
[58] Field of Search .......................................... 260/571

[56] References Cited

U.S. PATENT DOCUMENTS 3,558,690  1/1971  Sallmann et al. .................... 260/571

FOREIGN PATENT DOCUMENTS 47-20220  1972  Japan.

Primary Examiner—John F. Niebling
Attorney, Agent, or Firm—Frishauf, Holtz, Goodman & Woodward

[57] ABSTRACT

Improved process for preparing anthranylaldehyde derivatives of formula:

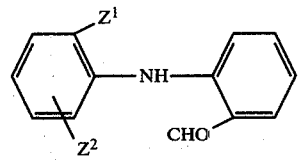

($Z^1$ and $Z^2$ each represents hydrogen atom, a halogen atom, methyl group or trifluoromethyl group.) is provided.

The process comprises steps of (1) protecting aldehyde group of a o-halogenobenzaldehyde with a specific alkylamine derivative, then (2) reacting the thus protected compound with a corresponding aniline derivative, and finally, (3) treating the thus obtained product with an acid.

The anthranylaldehyde derivatives, i.a. N-(2,6-dichlorophenyl)anthranylaldehyde is useful as an intermediate for preparation of the corresponding anilinophenylacetic acids which are anti-inflammatory and analgesic agents.

7 Claims, No Drawings

PROCESS FOR PREPARING ANTHRANYLALDEHYDE DERIVATIVES

BACKGROUND OF THE INVENTION

This invention relates to a novel process for preparing anthranylaldehyde derivatives More particularly, it relates to a process for preparing anthranylaldehyde derivatives of following formula (I):

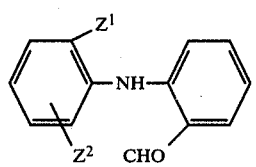

wherein $Z^1$ and $Z^2$ are same or different each other and each represent a hydrogen atom, a halogen atom, a methyl group or a trifluoromethyl group, $Z^1$ is attached to ortho position to the amino group and $Z_2$ may be positioned at any of 3-, 4-, 5- and 6-positions.

Compounds of formula (I) are expected to be used in various organic reactions as they have an aldehyde group, and therefore, it is quite important to develop an advantageous process for preparing the same. Among compounds of formula (I) obtained by the process of the invention, N-(2,6-dichlorophenyl)anthranylaldehyde having following formula (II) is an important material for preparing o-(2,6-dichloroanilino)phenylacetic acid having formula (III) (hereinafter referred to as "Dichlofoenac"), known as an anti-inflammatory and analgesic agent.

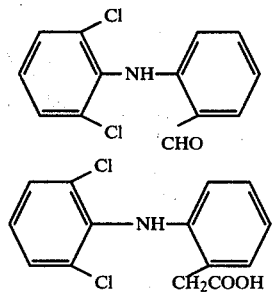

Known processes for the production of compound (III) include, for instance, those disclosed in Japanese Pat. Nos. 42-23418, 44-27374, 44-27573 and 45-11295. None of these methods, however, involves the aldehyde (II) as the starting material. The applicant has already developed a process for preparing Dichlofenac by using the aldehyde (II) as the starting material in Japanese patent application Nos. 51-142430 and 52-112210.

Heretofore, very few reports may be found regarding process for preparing aldehydes of formula (I), particularly aldehyde (II), with an exception of Japanese Pat. No. 47-20220 wherein there are disclosed a method of reducing N-(2,6-dichlorophenyl)anthranylic acid, a method of oxidizing o-(2,6-dichloroanilino)benzyl alcohol and a method of reducing N-(2,6-dichlorophenyl)anthranylic halide. The Specification, however, discloses no yield of the aldehyde (II).

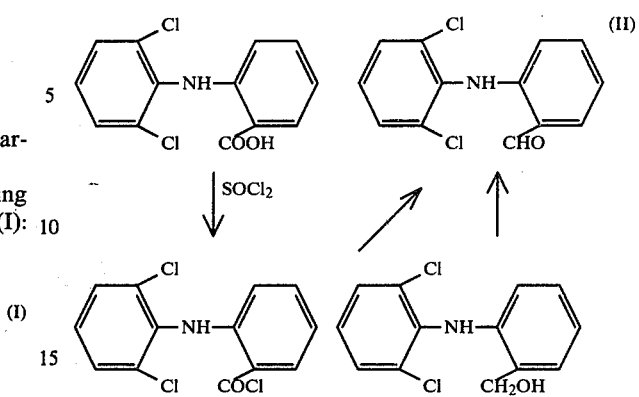

The inventors have tried to produce the desired compound (I) directly by the condensation reaction of o-halogenobenzaldehyde with an aniline derivative having following formula (IV) but failed to succeed.

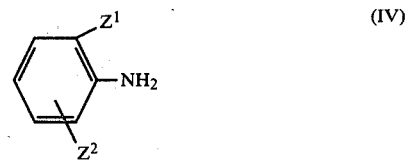

(wherein, $Z^1$ and $Z^2$ are as defined above).

After further studies, the inventors have found that a condensation product may be formed in good yield by using an o-halogenoaldehyde, the aldehyde group of which is protected with a specific group, and that the protected group may readily be converted to free aldehyde group with an acid.

BRIEF SUMMARY OF THE INVENTION

It is, therefore, an object of the invention to provide a compound (I) in good yield.

Other objects of the invention will become clear as the description proceeds.

According to the method of the invention, compounds (I) may be prepared by reacting on o-halogenobenzaldehyde having formula (V):

(wherein, X represents a halogen atom) with an alkylamine derivative having formula (VI):

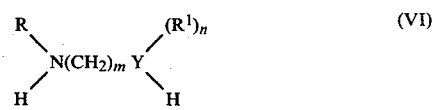

(wherein, R and $R^1$ each represent a lower alkyl group; Y represents nitorgen, oxygen or sulfur atom; m represents an integer of 2 or 3; and n represents 0 or 1, provided that n is 1 when Y is nitrogen atom and n is 0 when Y is oxygen or sulfur atom) to give a compound of formula (VII):

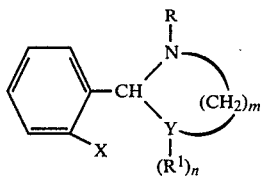

(wherein, X, Y, R, $R^1$, m and n are as defined above), then by reacting the compound (VII) with an aniline derivative (IV), and finally by treating the thus obtained product with an acid.

DETAILED DESCRIPTION OF THE INVENTION

In the above formulae, X represents a halogen atom, preferably bromine or iodine atom.

o-Halogenobenzaldehydes include o-chlorobenzaldehyde, o-bromobenzaldehyde and o-iodobenzaldehyde.

In alkylamine derivatives (VI), R and $R^1$ each represent a lower alkyl group having from 1 to 5 carbon atoms, such as methyl, ethyl, propyl and butyl. Examples of alkylamine derivatives (VI) are diamines such as N,N'-dimethylethylenediamine, N,N'-diethylethylenediamine, N,N'-dipropylethylenediamine and N,N'-dimethyl-1,3-propanediamine; aminoalcohols such as N-methylaminoethanol, N-ethylaminoethanol, N-propylaminoethanol and N-methylamino-3-propanol; and aminothiols such as n-methylaminoethylthiol, N-ethylaminoethylthiol, N-propylaminoethylthiol and N-methylamino-3-propylthiol.

The condensation reaction of o-halogenobenzaldehyde (V) with amine derivative (VI) may be performed by mixing them at ambient temperature and then by heating them in a solvent capable of forming an azeotropic mixture with water, while removing the water formed in situ.

Examples of solvents capable of forming an azeotropic mixture are benzene and toluene.

The condensation reaction proceeds almost quantitatively.

The subsequent condensation reaction of the compound (VII) with aniline derivative (IV) is performed in the presence of a base and a copper compound. There is no specific limitation as to the nature of base to be used in the process of the invention as far as it acts as a usual hydrogen halide eliminating agent. The base includes alkali carbonates such as sodium carbonate and potassium carbonate and alkali hydrogen carbonates such as sodium hydrogen carbonate and potassium hydrogen carbonate. Copper catalyst includes copper powder; various copper salts such as cuprous chloride, cupric chloride, cuprous bromide, curpic bromide and cuprous iodide; copper oxides such as cuprous oxide and cupric oxide; copper compounds with organic acids such as copper acetate; and copper chelate compounds such as acetylacetonatocopper.

Although the reaction may be performed in the absence of a solvent, it is preferable to employ a solvent in order to control the reaction temperature. The solvent includes non-polar solvent, for example, saturated hydrocarbons such as octane and nonane and aromatic hydrocarbons such as benzene and toluene. It also includes ethers such as dinormalhutyl, either diisobutyl ether, diisoamyl ether, ethyl amyl ether and anisole; and dimethylformamide and dimethyl sulfoxide. The reaction may be promoted in the presence of a tertiary amine, for example, N-alkylmorpholines such as N-methylmorpholine, N-ethylmorpholine, N-propylmorpholine and N-butylmorpholine.

The reaction may be promoted by refluxing a reaction mixture at a boiling point of the solvent used, and by removing water formed from an azeotropic mixture.

The period required for completion of the reaction will vary, depending on various conditions such as amount of catalyst to be used, species of solvent and molar ratio of reactants; but it will be suitably from 4 to 14 hours.

The reaction may preferably be performed at 80°–180° C.

Equimolar amounts of compound (VII) and aniline compound (IV) are used, in general. However, it is preferable that a little excess of aniline compound (IV) is used than the compound (VII).

The condensation product obtained by the above reaction has the following structure (VIII):

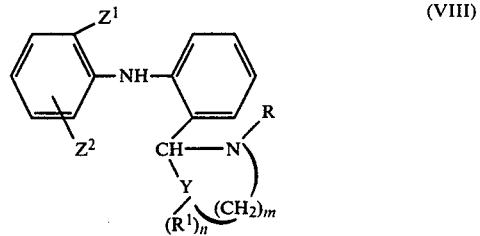

(wherein, Y, $Z^1$, $Z^2$, R, $R^1$, m and n are as defined above).

The compound (VIII) may react with excess aniline compound (IV) by further heating, giving a compound of the following formula (IX):

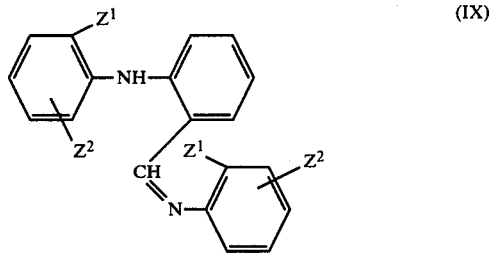

(wherein, $Z^1$ and $Z^2$ are as defined above).

The compound (IX) also gives the aimed anthranylaldehyde derivative (I) by treating it with an acid.

After the condensation reaction, the compound (VIII) may be isolated by conventional methods. For example, the solid residue is removed by filtration, the solvent is evaporated by distillation under reduced pressure, and crystals are separated. The yield of the condensation reaction is usually from 65 to 95%.

The compound (VIII) may readily be decomposed by maintaining it in a water-miscible organic solvent or aqueous solvent at an acidic condition to give the desired anthranylaldehyde derivative (I).

There is no specific limitation as to the nature of the organic solvent or aqueous solvent as far as it dissolves the compound (VIII).

Acid to maintain acidic condition includes inorganic acids such as hydrochloric acid, sulfuric acid and phosphoric acid; acidic salts such as sodium hydrogen sulfate, sodium hydrogen sulfite and ammonium chloride; and strong organic acids such as sulfonic acids and monochloroacetic acid.

The reaction usually proceeds at ambient temperature; but heating at 40°-70° C. is sometimes required, depending on the species of compounds to be decomposed.

The period required for completion of the reaction will vary from 10 minutes to 5 hours, preferably from 20 minutes to 1 hour.

Usually, the reaction is performed at ambient temperature under stirring for period mentioned above.

After completion of the reaction, the reaction mixture is extracted with a solvent such as benzene. Subsequently, the extract is dried and the solvent is removed to give compound (I) in the form of an oil or solid.

As mentioned above, the compound (VIII) may once be isolated for acid decomposition. Alternatively, compound (I) may also be obtained by acidifying the reaction mixture without isolation of compound (VIII).

As clear from the foregoing descriptions, the process of the invention provides anthranylaldehyde derivative (I) by using a readily available o-halogenobenzaldehyde as the starting material, with high yield, under quite easy operations.

The invention is further illustrated by the following working examples, which by no means restrict the scope of the invention.

EXAMPLE 1

9.0 g (0.01 mol.) of N,N'-dimethylethylenediamine was added dropwise to a solution of 18.5 g (0.10 mol.) of o-bromobenzaldehyde in 50 ml of toluene at 30°-40° C., and the mixture was stirred for 2 hours at ambient temperature.

Water was removed by azeotropic distillation with benzene, and the benzene was evaporated by distillation under reduced pressure. The resulting residue was distilled at 78°-81° C./0.4 mmHg, in a stream of nitrogen, affording 23.8 g of a pale yellow oil, which was confirmed to be 1,3-dimethyl-2-(o-bromophenyl)imidazolidine by IR (dissipation of carbonyl absorption of starting material) and NMR analyses. yield=93%.

NMR (CDCl$_3$): δ2.20 s (6H), 2.30–3.45 m (4H), 4.03 s (1H), 6.90–7.80 m (4H).

EXAMPLE 2

12.7 g of 1,3-dimethyl-2-(o-bromophenyl)imidazolidine (0.050 mol.), 16.2 g (0.10 mol.) of 2,6-dichloroaniline, 30 ml of N-isobutylmorpholine, 22.0 g (0.16 mol.) of pulverized potassium carbonate and 1.2 g (0.015 mol.) of cupric oxide were added to 50 ml of n-nonane. The mixture was refluxed for 6.5 hours, while removing water formed in situ by azeotropic distillation. After cooling and filtration, the n-nonane, N-isobutylmorpholine and 2,6-dichloroaniline were evaporated by distillation under reduced pressure of 0.5 mmHg, leaving a residue. The residue was dissolved in hot hexane, treated with charcoal and recrystallized, giving 13.5 g of pale yellow crystals. The compound was confirmed to be 1,3-dimethyl-2-[o-(2,6-dichloroaniline)phenyl]imidazolidine by IR, NMR and mass spectrometric analyses. yield=80%.

m.p.=114°–116° C.

IR (KBr): 2950–2600, 1596, 1530, 1460, 1350, 895, 770, 745, 710 cm$^{-1}$.

NMR (CDCl$_3$): δ2.27 s (6H), 2.50–3.40 m (4H), 3.54 s (1H), 6.30–7.45 m (7H).

MS (20 eV): m/e 337 (M$^+$+2, 36.9%), 336 (M$^+$+1, 26.0%), 335 (M$^+$, 57.7%), 334 (28.4%), 332 (65.0%), 321 (13.9%), 320 (base peak), 293 (40.7%), 292 (8.3%), 291 (67.4%).

EXAMPLE 3

3.4 g (0.010 mol.) of 1,3-dimethyl-2[o-(2,6-dichloroanilino)phenyl]imidazolidine obtained in Example 2 was dissolved in 30 ml of benzene. 10 ml of a 5% hydrochloric acid was added and the mixture was stirred for 30 minutes at ambient temperature. After separating the two layers, the benzene layer was dried with anhydrous sodium sulfate and the benzene was evaporated by distillation, leaving yellow crystals. The crystals were recrystallized from hexane to give 2.5 g of pale yellow crystals which were confirmed to be N-(2,6-dichlorophenyl)anthranylaldehyde by IR and NMR analyses. yield=94%.

m.p.=110°–112° C.

IR (KBr): 1665, 1590, 1508, 1455, 1400, 772, 752 cm$^{-1}$.

NMR (CDCl$_3$): δ62.5–7.60 m (7H), 9.85 s (1H).

EXAMPLE 4

9.0 g (0.10 mol.) of N,N'-dimethylethylenediamine was added to a solution of 18.5 g (0.10 mol.) of o-bromobenzaldehyde in 50 ml of xylene, and the mixture was stirred for 2 hours at ambient temperature. Then the mixture was heated and water formed in the system was removed by azeotropic distillation. The xylene solution was cooled and 32.4 g (0.20 mol.) of 2,6-dichloroaniline, 30 ml of N-ethylmorpholine and 30 g (0.22 mol.) of pulverized anhydrous potassium carbonate were added. The mixture was again heated for 2 hours to remove water by azeotropic distillation. After cooling, 2.8 g (0.020 mol.) of cuprous oxide was added and the mixture was refluxed for 6 hours, while removing water formed in situ by azeotropic distillation. After cooling and filtration, 100 ml of xylene was further added and then 50 ml of a 5% hydrochloric acid was added, and the mixture was stirred for 1 hour at 30°-40° C. The xylene layer was separated, washed with water, dried over anhydrous sodium sulfate and subjected to distillation under reduced pressure at 160°-168° C./0.4 mmHg to give 16.8 g of a yellow oil. After allowing to stand at ambient temperature, the oil turned to crystals which were confirmed to be N-(2,6-dichlorophenyl)anthranylaldehyde by IR and NMR analyses. yield=63%.

EXAMPLE 5

18.5 g (0.10 mol.) of o-bromobenzaldehyde was added to a solution of 9.0 g (0.10 mol.) of N,N'-dimethylethylenediamine in 50 ml of xylene, and the mixture was stirred for 2 hours at ambient temperature. The mixture was then heated to remove water in the system by azeotropic distillation.

The xylene solution was cooled and 64.8 g (0.40 mol.) of 2,6-dichloroaniline, 30 ml of N-isobutylmorpholine and 45 g (0.33 mol.) of pulverized anhydrous potassium carbonate were added.

The mixture was heated, with stirring, for 2 hours again to remove water in the system by azeotropic distillation. After cooling, 2.4 g (0.030 mol) of cupric oxide was added, and the mixture was refluxed for 4 hours, while removing water formed in situ by azeotropic distillation.

The mixture was cooled to 40° C., and excess amount of potassium carbonate and potassium bromide formed were dissolved by addition of 200 ml of water and stirring. The organic layer was separated and evaporated by distillation under reduced pressure. The bath temperature was maintained at 140° C. and the pressure was slowly reduced to remove a fraction distilled out at 0.5 mmHg. The residue was dissolved in 150 ml of benzene, and after addition of 50 ml of a 5% hydrochloric acid, the mixture was stirred and separated. The benzene layer was dried with anhydrous sodium sulfate and the benzene was evaporated by distillation under reduced pressure. The residue was recrystallized from hexane, affording 19.2 g of N-(2,6dichlorophenyl)anthranylaldehyde. yield=72%.

EXAMPLE 6

Following substantially the same procedures as in Example 4, except that 1.4 g (0.01 mol.) of cuprous bromide was used in place of cuprous oxide, there was obtained 10.2 g of N-(2,6-dichlorophenyl))anthranylaldehyde. yield=38%.

EXAMPLE 7

9.3 g (0.050 mol.) of o-bromobenzaldehyde was added to a solution of 6.0 g (0.052 mol.) of N,N'-diethylethylenediamine in 30 ml of xylene, and the mixture was stirred for 5, hours at ambient temperature. The mixture was heated to remove water in the system by azeotropic distillation. The xylene solution was cooled and 16.2 g (0.10 mol.) of 2,6-dichloroaniline, 15 ml of N-isobutylmorpholine and 15 g (0.11 mol.) of pulverized anhydrous potassium carbonate were added. The mixture was again heated for 2 hours to remove water in the system by azeotropic distillation. After cooling, 1.4 g (0.010 mol.) of cupric oxide was added and the mixture was refluxed for 15 hours to remove water formed in situ. By subjecting the reaction mixture to acid decomposition in the similar manner as in Example 5, there was obtained 7.5 g of N-(2,6-dichlorophenyl)anthranylaldehyde. yieldl=56%.

EXAMPLE 8

9.3 g of o-bromobenzaldehyde (0.050 mol.) was added to a solution of 3.8 g (0.050 mol.) of N-methylaminoethanol in 30 ml of xylene, and the mixture was stirred for 8 hours at ambient temperature. The mixture was heated to remove water in the system by azeotropic distillation. The xylene solution was cooled and 16.2 g (0.10 mol.) of 2,6-dichloroaniline, 15 ml of N-isobutylmorpholine and 22 g (0.16 mol.) of pulverized anhydrous potassium carbonate were added. The mixture was refluxed for 2 hours to remove water in the system by azeotropic distillation. After cooling, 1.2 g (0.015 mol.) of cupric oxide was added and the mixture was refluxed for 7.5 hours to remove water formed in situ. By subjecting the reaction mixture to acid decomposition in the similar procedures as in Example 5, there was obtained 6.5 g of N-(2,6-dichlorophenyl)anthranylaldehyde. yield=49%.

EXAMPLE 9

23.1 g (0.10 mol.) of o-iodobenzaldehyde was added to a solution of 9.0 g (0.10 mol.) of N,N'-dimethylethylenediamine in 50 ml of toluene, and the mixture was stirred for 8 hours at ambient temperature. The mixture was heated to remove water in the system by azeotropic distillation. The xylene solution was cooled and 48.6 g (0.30 mol.) of 2,6-dichloroaniline, 30 ml of N-isobutylmorpholine and 30 g (0.22 mol.) of pulverized anhydrous potassium carbonate were added. The mixture was again heated for 2 hours to remove water in the system by azeotropic distillation. After cooling, 2.4 g (0.030 mol.) of cupric oxide was added and the mixture was refluxed to remove water formed in situ. By subjecting the reaction mixture to acid decomposition in the similar manner as in Example 4, there was obtained 20 g of N-(2,6-dichlorophenyl)anthranylaldehyde. yield=75%.

EXAMPLE 10

A mixture of 92.5 g (0.50 mol.) of o-bromobenzaldehyde and 41.3 g (0.55 mol.) of N-methylaminoethanol in 300 ml of benzene was refluxed for 2 hours, while removing water formed in situ. The benzene was evaporated by distillation under reduced pressure, and the residue was subjected to distillation at 100°–102° C./1.0 mmHg under nitrogen stream to give 115.0 g of a colorless oil. The compound was confirmed to be 2-(o-bromophenyl)-3-methyloxazolidine by IR analysis on the basis of dissipation of carbonyl absorption shown in the starting material. yield=95%.

NMR (CDCl$_3$): δ2.30 s (3H), 2.45–3.37 m (2H), 3.87–4.10 m (2H), 5.15 s (1H), 6.90–7.70 m (4H). EXAMPLE 11

A mixture of 24.2 g (0.10 mol.) of 2-(o-bromophenyl)-3-methyloxazolidine, 32.4 g (0.20 mol.) of 2,6-dichloroaniline, 41.4 g (0.30 mol.) of pulverized anhydrous potassium carbonate and 2.4 g (0.030 mol.) of cupric oxide in 150 ml of di-n-butyl ether was refluxed for 6.5 hours, with vigorous stirring, while removing water formed in situ. After cooling and filtration, 100 ml of a 15% hydrochloric acid was added to the filtrate and the mixture was heated for 2 hours at 80°–85° C., with stirring. After cooling, the organic layer was separated and subjected to distillation under reduced pressure to remove the di-n-butyl ether and 2,6-dichloroaniline. The resulting residue was added to methanol to precipitate 17.3 g of the desired N-(2,6-dichlorophenyl)anthranylaldehyde in the form of pale yellow crystals. The filtrate was condensed and 15 ml of di-n-butyl ether was added, and the mixture was allowed to stand for 3 days, giving further 7.9 g of N-(2,6-dichlorophenyl)anthranylaldehyde. yield=72%.

EXAMPLE 12

A mixture of 48.4 g (0.20 mol.) of 2-(o-bromophenyl)-3-methyloxazolidine, 51.0 g (0.40 mol.) of o-chloroaniline, 83.0 g (0.60 mol.) of pulverized anhydrous potassium carbonate and 4.8 g (0.06 mol.) of cupric oxide in 350 ml of di-n-butyl ether was refluxed for 7 hours, with vigorous stirring, while removing water formed in situ. After cooling and filtration, the filtrate was washed with water, dried over anhydrous sodium sulfate and subjected to distillation, maintaining the bath temperature at 140° C. The pressure was gradually reduced and a fraction evaporated at 0.5 mmHg was separated.

The residue was dissolved in 130 ml of toluene, 40 ml of a 8% hydrochloric acid was added, and the mixture was heated for 2 hours at 60°–70° C. with stirring. After cooling, aqueous ammonia was added until pH of the aqueous layer reached 3–5 and the mixture was shaken. The toluene layer was separated, washed in turn with water, a 10% aqueous sodium hydrogen sulfite solution and water and dried over anhydrous sodium sulfate.

The toluene was evaporated by distillation under reduced pressure and the residue was subjected to distillation under reduced pressure at 172°–178° C./0.7–0.8 mmHg, affording 19.4 g of N-(o-chlorophenyl)enthranylaldehyde in the form of a pale yellow oil, the chemical structure of which was confirmed by IR and NMR analyses. yield=42%.

IR (neat): 3250, 1660, 1530, 1320, 742, 650 cm⁻¹.
NMR (CDCl₃): δ6.65–7.70 m (8H), 9.84 (1H).

EXAMPLE 13

Following substantially the same procedures as in Example 12, except that 65 g (0.40 mol.) of m-trifluoromethylaniline and 51.0 g (0.20 mol.) of 1,3-dimethyl-2-(o-bromophenyl)imidazolidine were used in place of o-chloroaniline and 2-(o-bromophenyl)-3-methyloxazolidine, respectively, there was obtained 26.6 g of N-(m-trifluoromethylphenyl)anthranylaldehyde, boiling at 150°–156° C./0.6 mmHg. yield=50%.

IR (KBr): 3250, 1660, 1580, 1332, 1120, 795, 750, 690 cm⁻¹.
NMR (CDCl₃): δ6.70–7.60 m (8H), 9.80 (1H).

EXAMPLE 14

Following similar procedures as in the first step of Example 12 and using 10.6 g (0.10 mol.) of o-toluidine and 12.7 g (0.050 mol.) of 1,3-dimethyl-2-(o-bromophenyl)imidazolidine, a mixture was refluxed for 4 hours. The reaction product was confirmed to be 1,3-dimethyl-2o-methylanilino)phenyl]o-methylanilino)-phenyl]imidazolidine by combined gas chromatographic and mass spectrometric analyses. The compound was then subjected to acid decomposition, giving N-(o-methylphenyl)anthranylaldehyde, the yield of which was 40% based on 1,3-dimethyl-2-(o-bromophenyl)imidazolidine reacted.

What is claimed is:

1. The process for preparing an anthranylaldehyde derivative of formula:

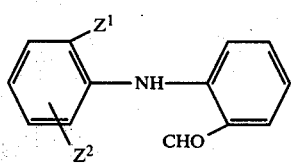

(wherein, Z¹ and Z² are same or different each other and each represent a hydrogen atom, a halogen atom, a methyl group or a trifluoromethyl group; Z¹ is attached to ortho position to the amino group and Z² may be positioned at any of 3-, 4-, 5- and 6-positions), which comprises steps of (1) reacting a o-halogenobenzaldehyde of the formula:

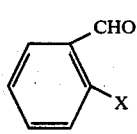

(wherein, X represents a halogen atom) with an alkylamine derivative of formula:

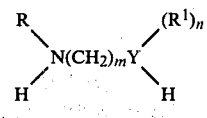

(wherein, R and R¹ each represents a lower alkyl group; Y represents a nitrogen, oxygen or sulfur atom; m represents an integer of 2 or 3; n represents 0 or 1, provided that n is 1 when Y is a nitrogen atom and n is 0 when Y is an oxygen or sulfur atom), affording a compound of formula:

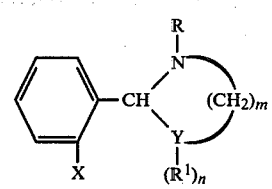

(wherein, X, R, R¹, m and n are as defined above),
(2) reacting the thus obtained compound with an aniline derivative of formula:

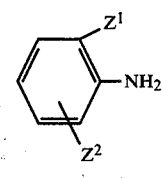

(wherein, Z¹ and Z² are as defined above), giving a condensation product, and,
(3) treating the thus obtained condensation product with an acid.

2. A process for preparing an anthranylaldehyde derivative of formula:

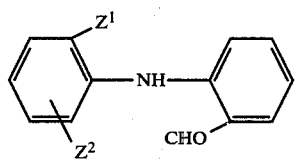

(wherein, Z¹ and Z² are same or different each other and each represent a hydrogen atom, a halogen atom, a methyl group or a trifluoromethyl group; Z¹ is attached to ortho position to the amino group and Z² may be positioned at any of 3-, 4-, 5- and 6-positions), which comprises steps of (1) reacting a compound of formula:

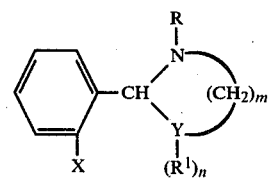

(wherein, R and R¹ each represent a lower alkyl group; Y represents a nitrogen, oxygen or sulfur atom; m represents an integer of 2 or 3; n represnts 0 or 1, provided that n is 1 when Y is a nitrogen atom and n is 0 when Y is an oxygen or sulfur atom) with an aniline derivative of formula:

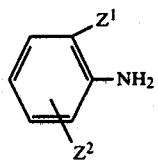

(wherein, $Z^1$ and $Z^2$ are as defined above), giving a condensation product, and, (2) treating the thus obtained condensation product with an acid.

3. The process according to claim 1 or 2, wherein Y is a nitrogen or oxygen atom and m is 2.

4. The process as claimed in claim 1 or 2, wherein the anthranylaldehyde derivative is N-(2,6-dihalophenyl)anthranylaldehyde.

5. The process as claimed in claim 4, wherein the N-(2,6-dihalophenyl)anthranylaldehyde is N-(2,6-dichlorophenyl)anthranylaldehyde.

6. The process as claimed in claim 1 or 2, wherein the anthranylaldehyde derivative is N-(m-trifluoromethylphenyl)anthranylaldehyde.

7. The process as claimed in claim 1 or 2, wherein the anthranylaldehyde derivative is N-(o-methylphenyl)anthranylaldehyde.

* * * * *

UNITED STATES PATENT AND TRADEMARK OFFICE
CERTIFICATE OF CORRECTION

PATENT NO. : 4,188,343
DATED : February 12, 1980
INVENTOR(S) : RYOZO SAKODA et al It is certified that error appears in the above—identified patent and that said Letters Patent are hereby corrected as shown below:

Column 9, lines 4-5:  replace "...enthranylaldehyde" with
---...anthranylaldehyde---.

Column 9, lines 32-33:  replace "1,3-dimethyl-2o-methyl-anilino)phenyl]o-methylanilino)phenyl]imidazolidine" with
---1,3-dimethyl-2-[o-(o-methylanilino)phenyl]-imidazolidine---.

Signed and Sealed this

Fourteenth Day of October 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,188,343
DATED : February 12, 1980
INVENTOR(S) : Ryozo Sakoda et al.

It is certified that error appears in the above—identified patent and that said Letters Patent is hereby corrected as shown below:

On the title page, Item [30] should read:

January 9, 1978     Japan [JP]     53/513

*Signed and Sealed this*

*Eighteenth* Day of *November 1980*

[SEAL]

*Attest:*

SIDNEY A. DIAMOND

*Attesting Officer*     *Commissioner of Patents and Trademarks*